US010948460B2

(12) United States Patent
Rudolf et al.

(10) Patent No.: US 10,948,460 B2
(45) Date of Patent: Mar. 16, 2021

(54) FLUID SENSOR ASSEMBLY

(71) Applicant: TE CONNECTIVITY CORPORATION, Berwyn, PA (US)

(72) Inventors: Zoltan Rudolf, Summerfield, NC (US); Romit Sarkar, Kernersville, NC (US)

(73) Assignee: TE CONNECTIVITY CORPORATION, Berwyn, PA (US)

( * ) Notice: Subject to any disclaimer, the term of this patent is extended or adjusted under 35 U.S.C. 154(b) by 206 days.

(21) Appl. No.: 16/214,348

(22) Filed: Dec. 10, 2018

(65) Prior Publication Data
US 2020/0182833 A1 Jun. 11, 2020

(51) Int. Cl.
| G01N 29/22 | (2006.01) |
| G01N 1/14 | (2006.01) |
| G01N 1/42 | (2006.01) |
| G01N 1/44 | (2006.01) |
| G01N 29/02 | (2006.01) |
| G01N 1/10 | (2006.01) |

(52) U.S. Cl.
CPC .............. *G01N 29/222* (2013.01); *G01N 1/14* (2013.01); *G01N 1/42* (2013.01); *G01N 1/44* (2013.01); *G01N 29/02* (2013.01); *G01N 2001/1037* (2013.01)

(58) Field of Classification Search
CPC .......... G01N 29/222; G01N 1/14; G01N 1/42; G01N 1/44; G01N 29/02; G01N 33/2835; G01F 23/74
See application file for complete search history.

(56) References Cited

U.S. PATENT DOCUMENTS

| 9,297,686 B1* | 3/2016 | Ross, Jr. ............... G01F 23/263 |
| 2011/0271754 A1 | 11/2011 | Ross, Jr. et al. |
| 2013/0064716 A1* | 3/2013 | Fukuoka ............. G01F 25/0069 |
| | | 422/106 |
| 2016/0123929 A1 | 5/2016 | Op De Beeck et al. |
| 2020/0232840 A1* | 7/2020 | Gismervik ............. F01N 3/208 |

OTHER PUBLICATIONS

Extended European Search Report, European Application No. 19213889. 9-1001, European Filing Date Apr. 27, 2020.

* cited by examiner

*Primary Examiner* — David Z Huang

(57) ABSTRACT

A fluid sensor assembly for sensing a fluid contained in a fluid tank of a vehicle includes a housing unit having a base plate, a sample suction line, and a sample return line. The fluid sensor assembly includes a header assembly having a header housing separably coupled to the housing unit. The header housing is located exterior of the fluid tank of the vehicle. The header assembly has a sample tank in fluid communication with the sample suction line and the sample return line. The sample tank receives fluid from the fluid tank and a fluid quality sensor senses a quality characteristic of the fluid in the sample tank for quality sampling of the fluid at a location remote from an interior of the fluid tank.

20 Claims, 2 Drawing Sheets

FLUID SENSOR ASSEMBLY

BACKGROUND OF THE INVENTION

The subject matter herein relates generally to fluid sensor assemblies.

In some applications, e.g. in a fueling system of an engine, or a DEF (Diesel Exhaust Fluid) delivery system of a SCR (Selective Catalytic Reduction) apparatus, fluid level needs to be maintained above a certain level, and fluid quality issues, such as impure fluid or diluted fluid, need to be detected for avoiding deterioration in system performance and damages to the system. In these applications, normally a fluid level sensor and a fluid quality sensor are used for measuring fluid level and monitoring fluid quality. For example, the fluid level sensor is a reed switch sensor in various systems and the fluid quality sensor includes an ultrasound sensor. The fluid level sensor and the fluid quality sensor are typically held by a fluid sensor housing in the fluid tank. Monitoring fluid quality in the fluid tank is difficult and may lead to inaccurate quality measurements. Additionally, the fluid sensors are integrated into a common sensor unit. Repair or replacement requires removing of the sensor unit and replacing the entire sensing unit. A need remains for a robust and cost effective fluid sensor assembly.

BRIEF DESCRIPTION OF THE INVENTION

In one embodiment, a fluid sensor assembly is provided for sensing a fluid contained in a fluid tank of a vehicle including a housing unit having a base plate configured to be coupled to the fluid tank. The housing unit includes a sample suction line and a sample return line configured to be in fluid communication with the fluid in the fluid tank. The fluid sensor assembly includes a header assembly having a header housing separably coupled to the housing unit. The header housing is configured to be located exterior of the fluid tank of the vehicle. The header assembly has a sample tank in fluid communication with the sample suction line and the sample return line. The sample tank is configured to receive fluid from the fluid tank. The header assembly includes a fluid quality sensor sensing a quality characteristic of the fluid in the sample tank for quality sampling of the fluid at a location remote from an interior of the fluid tank.

In another embodiment, a fluid sensor assembly is provided for sensing a fluid contained in a fluid tank of a vehicle including a housing unit having a base plate configured to be coupled to the fluid tank. The housing unit includes a sample suction line and a sample return line configured to be in fluid communication with the fluid in the fluid tank. The fluid sensor assembly includes a fluid level sensor assembly separably coupled to the housing unit including a level sensor determining a fluid level of the fluid in the fluid tank, the fluid level sensor assembly including a fluid level sensor connector. The fluid sensor assembly includes a header assembly having a header housing separably coupled to the housing unit. The header housing is configured to be located exterior of the fluid tank of the vehicle. The header assembly has a sensor connector coupled to the fluid level sensor connector to receive data from the fluid level sensor assembly relating to the fluid level measured by the fluid level sensor. The header assembly has a sample tank in fluid communication with the sample suction line and the sample return line. The sample tank is configured to receive fluid from the fluid tank. The header assembly includes a fluid quality sensor sensing a quality characteristic of the fluid in the sample tank for quality sampling of the fluid at a location remote from an interior of the fluid tank.

In a further embodiment, a fluid sensor assembly is provided for sensing a fluid contained in a fluid tank of a vehicle including a housing unit having a base plate configured to be coupled to the fluid tank. The housing unit includes a sample suction line and a sample return line configured to be in fluid communication with the fluid in the fluid tank. The fluid sensor assembly includes a temperature control device coupled to the housing unit and configured to extend into the fluid tank. The temperature control device is configured to be in thermal communication with the fluid in the fluid tank to affect a temperature of the fluid in the fluid tank. The fluid sensor assembly includes a header assembly having a header housing separably coupled to the housing unit. The header housing is configured to be located exterior of the fluid tank of the vehicle. The header assembly has a sample tank in fluid communication with the sample suction line and the sample return line. The sample tank is configured to receive fluid from the fluid tank. The header assembly includes a fluid quality sensor sensing a quality characteristic of the fluid in the sample tank for quality sampling of the fluid at a location remote from an interior of the fluid tank.

DETAILED DESCRIPTION OF THE INVENTION

Figure 1:
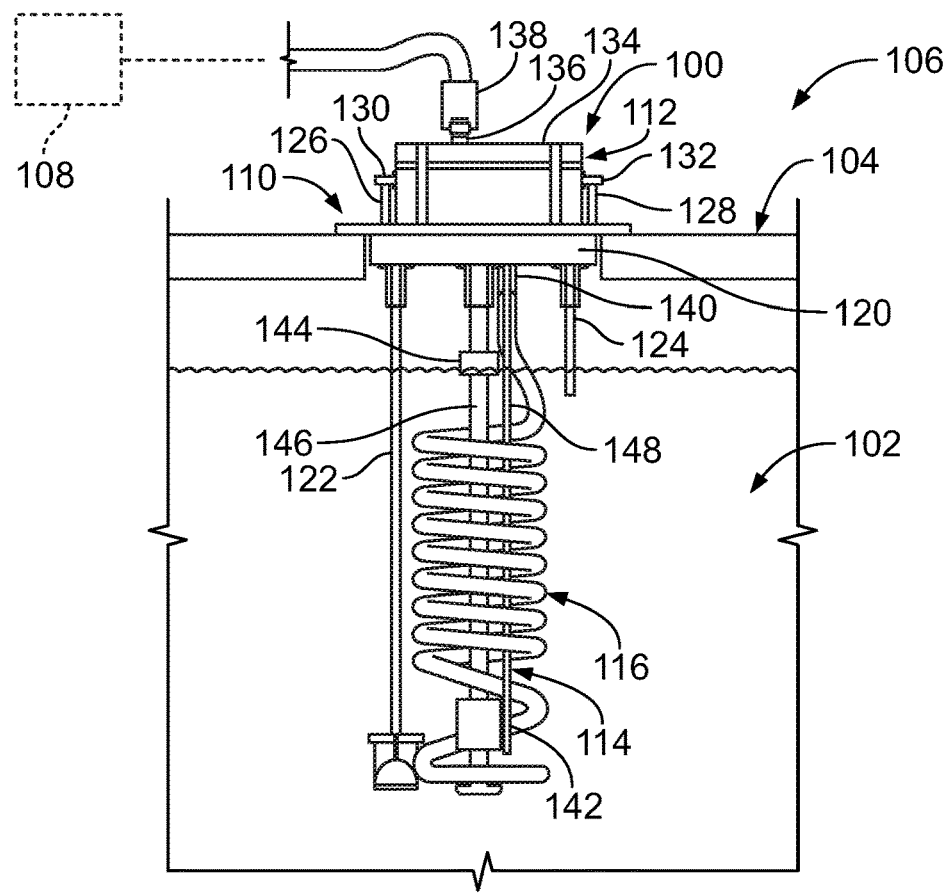
FIG. 1 is a schematic view of a fluid sensor assembly in accordance with an exemplary embodiment.

FIG. 1 is a schematic view of a fluid sensor assembly 100 for sensing a fluid 102 contained in a fluid tank 104 of a vehicle 106. The vehicle 106 may be an automotive vehicle, and agricultural vehicle, an aircraft, a Marine vehicle, and the like. The fluid sensor assembly 100 may sense one or more fluid characteristics of the fluid 102. For example, the fluid sensor assembly 100 may sense concentrations of one or more substances in the fluid 102. The fluid sensor assembly 100 may sense contaminations in the fluid 102. The fluid sensor assembly 100 may sense other fluid characteristics, such as temperature, viscosity, density, and the like. The fluid 102 may be fuel, oil, hydraulic fluid, transmission fluid, or another type of fluid. In various embodiments, the fluid 102 is diesel exhaust fluid (DEF) and the fluid sensor assembly 100 is a DEF quality sensor. The DEF quality sensor may sense quality of urea or other reduction agents in the DEF fluid.

In an exemplary embodiment, the fluid sensor assembly 100 is connected to a vehicle system 108 of the vehicle 106. For example, the fluid sensor assembly 100 may be electrically connected to the vehicle system 108 for communicating data relating to the fluid quality of the fluid 102 to the vehicle system 108. The fluid sensor assembly 100 may be electrically connected to the vehicle system 108 for powering one or more components of the fluid sensor assembly 100. The fluid sensor assembly 100 may be coupled to other types of vehicle systems, such as a coolant system of the vehicle 106 for heating the fluid 102 in the fluid tank 104.

In an exemplary embodiment, the fluid sensor assembly 100 includes a housing unit 110, a header assembly 112, a fluid level sensor assembly 114 and a temperature control device 116. The housing unit 110 includes a base plate 120 configured to be coupled to the fluid tank 104. In an exemplary embodiment, the header assembly 112 is separably coupled to the base plate 120 of the housing unit 110. For example, the header assembly 112 may be removable and replaceable relative to the housing unit 110. In an exemplary embodiment, the fluid level sensor assembly 114 is separably coupled to the base plate 120 of the housing unit 110. For example, the fluid level sensor assembly 114 may be removable and replaceable relative to the housing unit 110. In an exemplary embodiment, the fluid level sensor assembly 114 is separably coupled to the header assembly 112. For example, the fluid level sensor assembly 114 may be removable and replaceable relative to the header assembly 112. In an exemplary embodiment, the temperature control device 116 is separably coupled to the base plate 120 of the housing unit 110. For example, the temperature control device 116 may be removable and replaceable relative to the housing unit 110. In an exemplary embodiment, the temperature control device 116 is separably coupled to the header assembly 112. For example, the temperature control device 116 may be removable and replaceable relative to the header assembly 112.

In an exemplary embodiment, a portion of the fluid sensor assembly 100 is located interior of the fluid tank 104 in contact with the fluid 102. For example, a portion of the housing unit 110 and/or a portion of the fluid level sensor assembly 114 and/or a portion of the temperature control device 116 may extend into the fluid tank 104 in contact with the fluid 102. In an exemplary embodiment, a portion of the fluid sensor assembly 100 is located exterior of the fluid tank 104 and is spaced apart from the fluid 102. For example, the header assembly 112 may be located exterior of the fluid tank 104. Optionally, the header assembly 112 may be removable from the housing unit 110 without removing the housing unit 110 from the fluid tank 104.

In an exemplary embodiment, the housing unit 110 includes a sample suction line 122 and a sample return line 124 configured to be in fluid communication with the fluid 102 in the fluid tank 104. Optionally, the sample suction line 122 and the sample return line 124 form a closed sample loop for circulating a sample of the fluid 102 through the fluid sensor assembly 100. The sample the fluid is returned to the fluid tank 104 after sampling. The fluid sensor assembly 100 is separate from the main suction line used to remove the fluid 102 from the fluid tank 104, such as for consumption of the fluid 102 during operation of the vehicle 106. The fluid sensor assembly 100 samples the fluid 102 from the fluid tank 104 rather than sampling fluid in the main suction line from the fluid tank 104. In an exemplary embodiment, the closed sample loop flows through the header assembly 112. For example, the housing unit 110 includes a suction line fitting 126 and a return line fitting 128 in flow communication with the sample suction line 122 and the sample return line 124, respectively. The header assembly 112 includes a corresponding suction line fitting 130 and a corresponding return line fitting 132 configured to be coupled to the suction line fitting 126 and the return line fitting 128 of the housing unit 110. The fittings 126, 128, 130, 132 are separable to allow the header assembly 112 to separate from the housing unit 110. The fittings 126, 128, 130, 132 may be sealed at the respective interfaces to allow connection and disconnection without losing or leaking the fluid 102 in the closed sample loop. The fittings 126, 128 may be male fittings or female fittings and the fittings 130, 132 may be male fittings or female fittings. In the illustrated embodiment, the suction lines 122, 124 are coupled to the base plate 120 and extend into the interior of the fluid tank 104 and the fittings 126, 128 are coupled to the base plate 120 at an exterior of the base plate 120 for interfacing with the header assembly 112. The fluid 102 passes between the interior of the fluid tank 104 and the exterior of the fluid tank 104 through the housing unit 110. For example, the fluid 102 may be sampled in the header assembly 112 exterior of the fluid tank 104 before being circulated back into the fluid tank 104 through the sample return line 124.

In an exemplary embodiment, the header assembly 112 includes a header housing 134 configured to be coupled to the base plate 120 of the housing unit 110. The header housing 134 may be coupled directly to the base plate 120 in various embodiments. In other alternative embodiments, the header housing 134 may be spaced apart from the base plate 120 at a remote location and connected to the housing unit 110 by one or more fluid lines for circulating the fluid between the housing unit 110 and the header assembly 112.

The header assembly 112 includes a vehicle connector 136 for interfacing with the vehicle system 108. For example, an electrical connector 138 of the vehicle system 108 is coupled to the vehicle connector 136. Electrical signals may be transmitted between the header assembly 112 in the vehicle system 108 through the vehicle connector 136 and the electrical connector 138. For example, data relating to the fluid quality characteristics measured by the fluid sensor assembly 100 may be transmitted to the vehicle system 108. Power may be supplied to the header assembly 112 through the electrical connector 138 and the vehicle connector 136.

In an exemplary embodiment, the header assembly 112 includes a sensor connector 140 configured to be electrically connected to the fluid level sensor assembly 114. The fluid level sensor assembly 114 is used to determine a fluid level of the fluid 102 and the fluid tank 104. Signals from the fluid level sensor assembly 114 may be transmitted to the header assembly 112 through the sensor connector 140. In an exemplary embodiment, the fluid level sensor assembly 114 includes a reed switch 142 used to sense fluid level of the fluid 102 and the fluid tank 104. The fluid level sensor assembly 114 may include multiple reed switches. In various embodiments, the fluid level sensor may include a float 144 in the fluid tank 104 on a float tube 146 that positions the float 144 in the fluid tank 104. The float 144 floats on top of the fluid 102. When the float 144 reaches the reed switch 142, the fluid level sensor assembly 114 may send a signal relating to a low fluid level in the fluid tank 104. For example, the reed switch 142 may be connected to a reed switch circuit board 148 electrically connected to the sensor connector 140. Other types of level sensors may be used in alternative embodiments for determining fluid level within the fluid tank 104. Other types of fluid level sensors may be used in alternative embodiments, such as a magneto resistive unit, an ultrasonic sensor, and the like.

In an exemplary embodiment, the temperature control device 116 is coupled to the base plate 120 of the housing unit 110. The temperature control device 116 extends into the fluid tank 104 and may be in thermal contact with the fluid 102. The temperature control device 116 may be operated to affect a temperature of the fluid 102 and the fluid tank 104. In an exemplary embodiment, the temperature control device 116 includes a heating element for heating the fluid 102. For example, the heating element may be an electrical heating element powered through the header assembly 112. In an exemplary embodiment, the temperature control device 116 includes a cooling element for cooling the fluid 102. For example, the cooling element may be a refrigerant line that circulates refrigerant through the fluid tank 104 to cool the fluid 102. The refrigerant line may be connected to a cooling system of the vehicle 106, such as through one or more fittings on the header assembly 112 and/or the base plate 120 of the housing unit 110.

In an exemplary embodiment, the fluid sensor assembly 100 is modular in design to allow repair and/or replacement of one or more of the elements of the fluid sensor assembly 100 without the need to replace other elements of the fluid sensor assembly 100. For example, the header assembly 112 may be removed and replaced with an upgraded header assembly 112 without replacing the housing unit 110 and/or the fluid level sensor assembly 114 and/or the temperature control device 116. The independent elements are separately manufacturable. The elements may be produced, tested and calibrated separately from each other and integrated together. The elements of the fluid sensor assembly 100 are field repairable and/or field replaceable. In an exemplary embodiment, the fluid sensor assembly 100 allows fluid sampling and testing remote from the fluid tank 104, such as in the header assembly 112 exterior of the fluid tank 104. The environmental conditions of the fluid may be more repeatably and consistently controlled during testing for more accurate testing. For example, the sample testing may be performed remote from harsh operating environments. For example, the temperature and the pressure of the fluid being sampled may be better controlled in the header assembly 112 exterior of the fluid tank 104 as opposed to in situ within the fluid tank 104.

Figure 2:
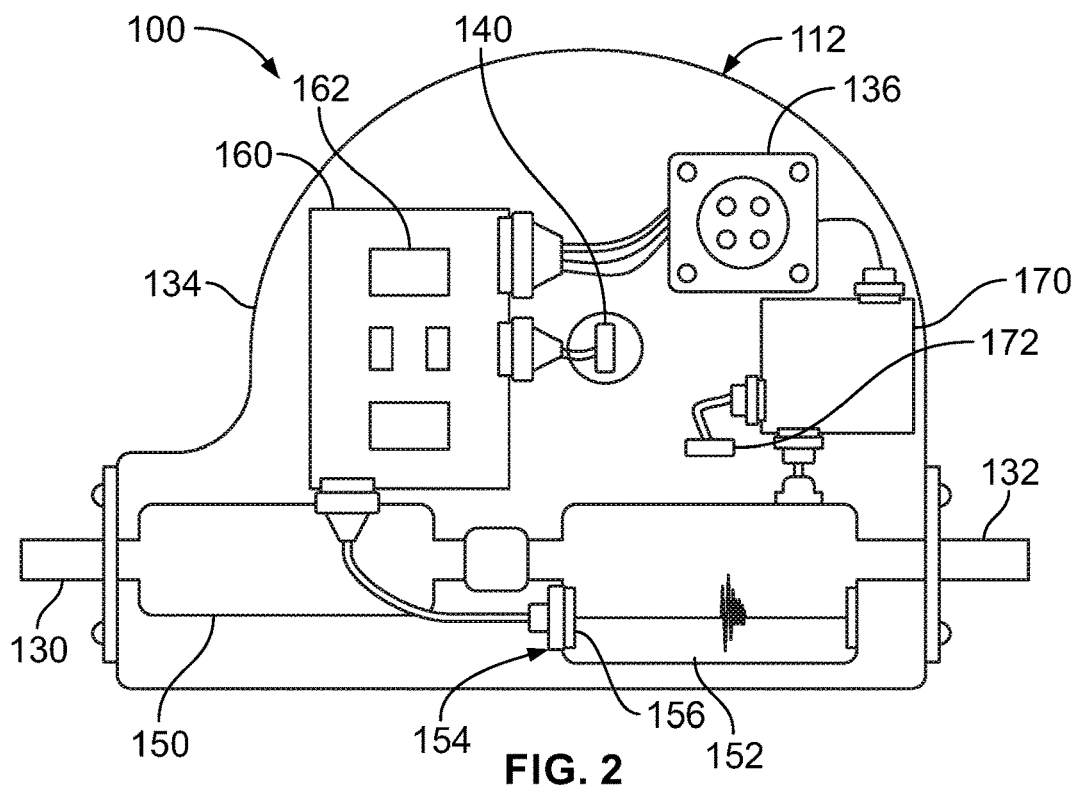
FIG. 2 is a schematic view of a header assembly of the fluid sensor assembly in accordance with an exemplary embodiment.

FIG. 2 is a schematic view of the header assembly 112 of the fluid sensor assembly 100 in accordance with an exemplary embodiment. The header assembly 112 includes components within the header housing 134. In an exemplary embodiment, the header housing 134 may be sealed to provide a sealed environment for the components and for fluid testing. The suction line fitting 130 and the return line fitting 132 extend from the header housing 134 for interfacing with the housing unit 110 to create a flow path for the fluid 102 through the header assembly 112. The vehicle connector 136 extends from the header housing 134 to create an electrical connection with the vehicle system 108 of the vehicle 106.

In an exemplary embodiment, the header assembly 112 includes a fluid pump 150 for circulating fluid through the header assembly 112. For example, the fluid pump 150 may be coupled to the suction line fitting 130 for pumping fluid through the system. The fluid pump 150 is used to control the pressure of the fluid in the closed sample loop for consistent sampling by the fluid sensor assembly 100. The fluid pump 150 may maintain a constant pressure in the sample loop such that sampling occurs at constant pressure. The fluid pump 150 is used to draw the fluid out of the fluid tank 104 into the header assembly 112. The fluid 102 in the sample loop may be bubble-free, which may enhance testing quality of the fluid 102. For example, the fluid pump 150 may pressurize the fluid 102 to eliminate any bubbles in the sample loop.

The header assembly 112 includes a sample tank 152 in fluid communication with the suction line fitting 130 and the return line fitting 132. In an exemplary embodiment, the sample tank 152 is in the header housing 134. Alternatively, the sample tank 152 may be located remote from the header housing 134 exterior of the fluid tank 104. The fluid 102 is circulated from the sample suction line 122 to the sample return line 124 through the sample tank 152 by the fluid pump 150. In an exemplary embodiment, the fluid is tested in the sample tank 152. As such, sampling of the fluid 102 occurs outside of the fluid tank 104, such as in the header housing 134 of the header assembly 112. The sample tank 152 may be a small controlled environment for testing the fluid. For example, the temperature may be controlled in the sample tank 152 generally independent of the temperature of the fluid in the fluid tank 104 because the sample tank is remote from the fluid tank 104. The sample tank may control pressure regulation in the sample tank 152 generally independent of the pressure of the fluid in the fluid tank 104 because the sample tank is remote from the fluid tank 104.

In an exemplary embodiment, the header assembly 112 includes a fluid quality sensor 154 in the header housing 134. The fluid quality sensor 154 tests the fluid 102 in the sample tank 152. The fluid quality sensor 154 may sense one or more fluid characteristics of the fluid 102. For example, the fluid quality sensor 154 may sense concentrations of one or more substances in the fluid 102. The fluid quality sensor 154 may sense contaminations in the fluid 102. The fluid quality sensor 154 may sense other fluid characteristics, such as temperature, viscosity, density, and the like. In an exemplary embodiment, the fluid quality sensor 154 includes an ultrasound transducer 156 for quality sampling of the fluid 102. Other types of sampling sensor may be provided in other various embodiments. The ultrasound transducer 156 may be located at or in the sample tank 152 for quality testing of the fluid 102. The ultrasound transducer 156 transmits ultrasound signals through the fluid 102 for testing one or more quality characteristics of the fluid. In other various embodiments, the fluid quality sensor 154 may include other types of sensing elements. For example, the fluid quality sensor 154 may include an infrared sensor configured to transmit infrared signals through the fluid in the sample tank 152. Optionally, the fluid quality sensor 154 may include different types of sensors for sensing different quality characteristics of the fluid.

In an exemplary embodiment, the header assembly 112 includes a sensor circuit board 160 having one or more sensor components 162 on the sensor circuit board 160. The sensor components 162 may be used for data processing of signals from the fluid quality sensor 154 to determine one or more quality characteristics of the fluid 102. The sensor components 162 may include one or more processes, memories, communication components, and the like. The fluid quality sensor 154 is electrically connected to the sensor circuit board 160, such as by wires, connectors, and the like. Operation of the fluid quality sensor 154 may be controlled by one or more sensor components 162 on the sensor circuit board 160. Data from the fluid quality sensor 154 may be analyzed by one or more sensor component 162 on the sensor circuit board 160. Data from the fluid quality sensor 154 may be transmitted by one or more sensor components 162 to another component, such as the vehicle connector 136 and/or the vehicle system 108.

In an exemplary embodiment, the sensor connector 140 is electrically connected to the sensor circuit board 160. Data from the fluid level sensor assembly 114 may be transmitted to one or more sensor components 162 on the sensor circuit board 160 through the sensor connector 140. Data from the fluid level sensor assembly 114 may be transmitted by one or more sensor components 162 to another component, such as the vehicle connector 136 and/or the vehicle system 108.

In an exemplary embodiment, the header assembly 112 includes a heating element circuit board 170 for controlling operation of a heating element 172 of the temperature control device 116. The heating element circuit board 170 may be electrically connected to the vehicle connector 136, such as for receiving power from the vehicle.

Figure 3:
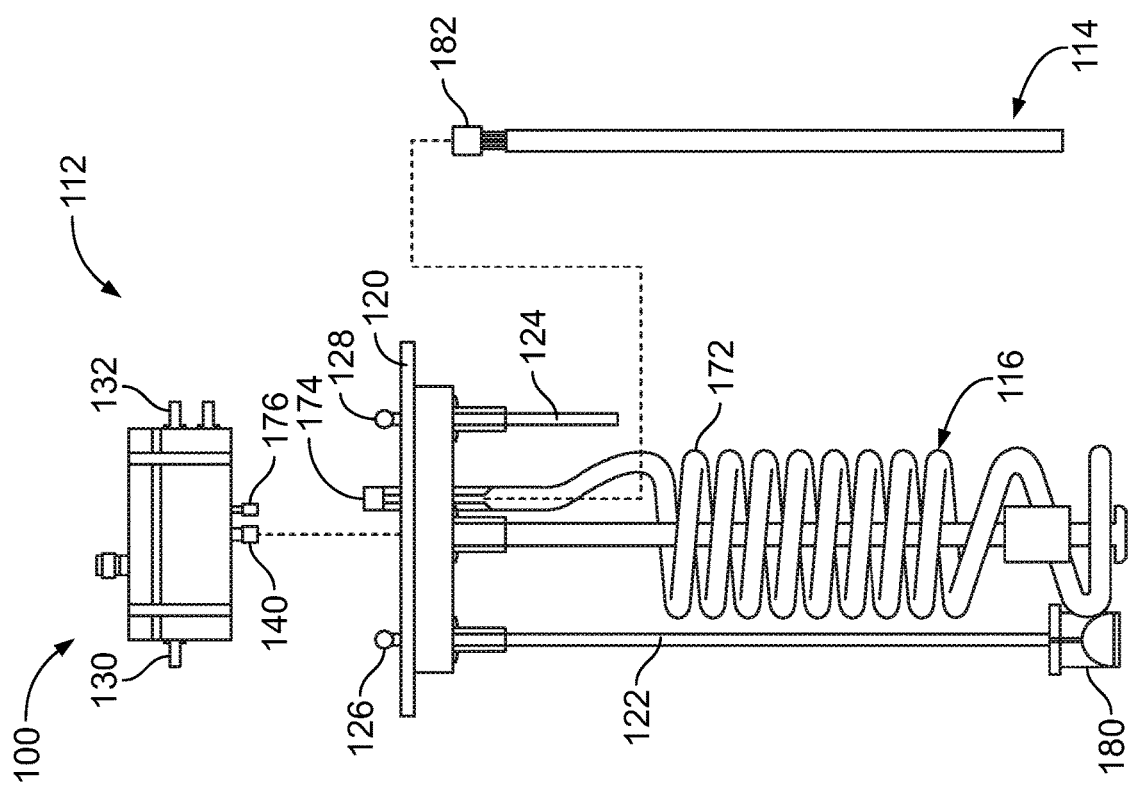
FIG. 3 is an exploded view of the fluid sensor assembly in accordance with an exemplary embodiment.

FIG. 3 is an exploded view of the fluid sensor assembly 100 in accordance with an exemplary embodiment. FIG. 3 illustrates the temperature control device 116 including the heating element 172. The heating element 172 includes a heating element connector 174 configured to be electrically connected to the header assembly 112. FIG. 3 illustrates the sample suction line 122 and sample return line 124 extending from a bottom of the base plate 120. In an exemplary embodiment, a filter 180 is provided on the sample suction line 122 to filter the fluid 102 mean circulated through the closed sample loop. FIG. 3 illustrates the suction line fitting 126 and the return line fitting 128 at a top of the base plate 120 for interfacing with the header assembly 112.

In an exemplary embodiment, the header assembly 112 is separately provided from the housing unit 110 and configured to be removably coupled to the housing unit 110. The suction line fitting 130 and the return line fitting 132 may be mated with the suction line fitting 126 and the return line fitting 128, respectively. The header assembly 112 includes a heating element connector 176 configured to be mated with the heating element connector 174 of the temperature control device 116, such as for supplying power to the temperature control device 116. The header assembly 112 includes the sensor connector 140 configured to be coupled to a fluid level sensor connector 182 of the fluid level sensor assembly 114. The header assembly 112 is removably coupled to the housing unit 110 such that the header assembly 112 may be replaced, such as when one or more components of the header assembly 112 are defective or in need of an upgrade. The header assembly 112 may be removed and replaced in the field without removing and/or replacing the housing unit 110.

In an exemplary embodiment, the fluid level sensor assembly 114 is separately provided from the housing unit 110 and configured to be removably coupled to the housing unit 110. The fluid level sensor connector 182 may be removably coupled to the sensor connector 140. For example, the fluid level sensor assembly 114 may be coupled to the base plate 120 and/or extend through the base plate 120 for interfacing with the header assembly 112.

Figure 4:
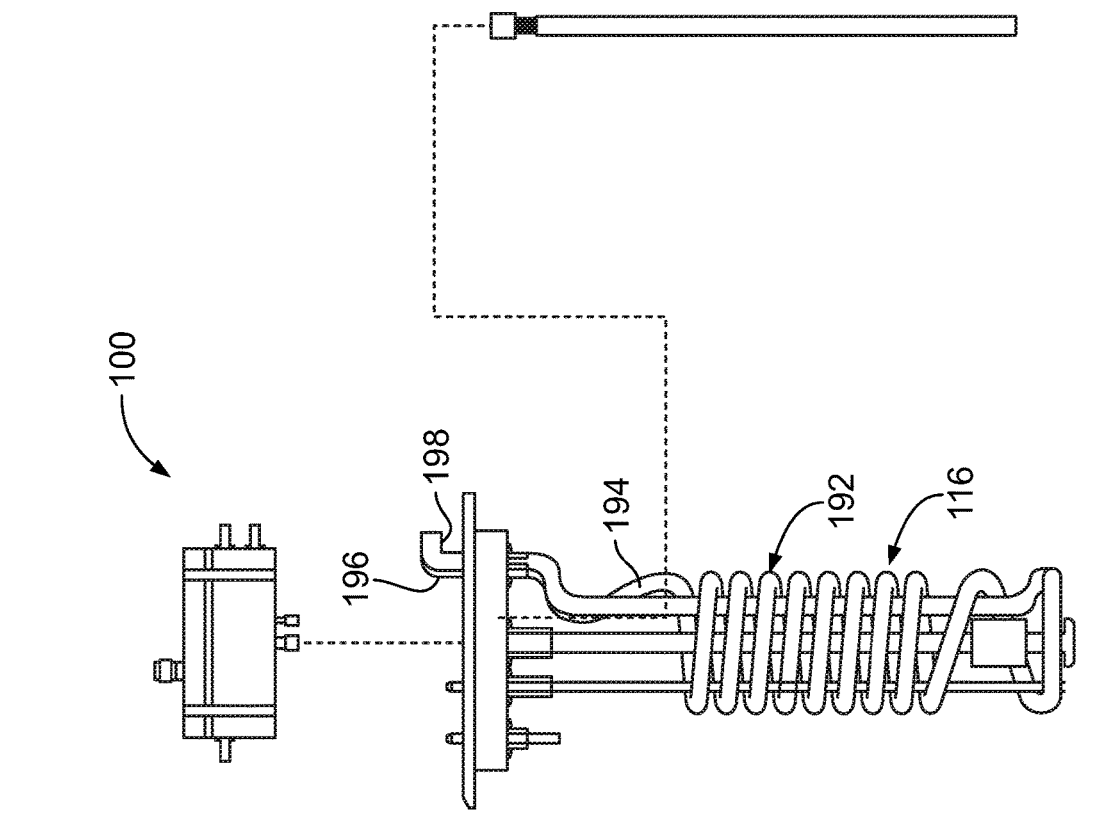
FIG. 4 is an exploded view of the fluid sensor assembly in accordance with an exemplary embodiment.

FIG. 4 is an exploded view of the fluid sensor assembly 100 in accordance with an exemplary embodiment. FIG. 4 illustrates the temperature control device 116 including a cooling element 192. The cooling element 192 includes a coolant line 194 having a supply fitting 196 and the return fitting 198. Coolant is circulated through the coolant line 194. The coolant line 194 is configured to be in thermal communication with the fluid 102 in the fluid tank 104 for heating the fluid 102, such as to prevent freezing of the fluid 102. Optionally, a heating element may be provided for heating the fluid.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A fluid sensor assembly for sensing a fluid contained in a fluid tank of a vehicle, the fluid sensor assembly comprising:
   a housing unit having a base plate configured to be coupled to the fluid tank, the housing unit including a sample suction line and a sample return line configured to be in fluid communication with the fluid in the fluid tank; and
   a header assembly having a header housing separably coupled to the housing unit, the header housing configured to be located exterior of the fluid tank of the vehicle, the header assembly having a sample tank in fluid communication with the sample suction line and the sample return line, the sample tank located exterior of the fluid tank and configured to receive fluid from the fluid tank, the header assembly including a fluid quality sensor sensing a quality characteristic of the fluid in the sample tank for quality sampling of the fluid at a location remote from an interior of the fluid tank.

2. The fluid sensor assembly of claim 1, wherein the header assembly is separable from the housing unit without removing the housing unit from the fluid tank.

3. The fluid sensor assembly of claim 1, wherein the header assembly is sealed.

4. The fluid sensor assembly of claim 1, wherein the sample tank is contained within the header housing.

5. The fluid sensor assembly of claim 1, wherein the housing unit includes a suction line fitting and a return line fitting, the header assembly including a suction line fitting removably coupled to the suction line fitting of the housing unit, the header assembly including a return line fitting removably coupled to the return line fitting of the housing unit.

6. The fluid sensor assembly of claim 1, wherein the sample suction line and the sample return line form a closed sample loop for sampling the fluid.

7. The fluid sensor assembly of claim 1, wherein the header assembly includes a vehicle connector configured to be connected to an electrical connector of the vehicle.

8. The fluid sensor assembly of claim 1, wherein the header assembly includes a pump in flow communication with the sample suction line.

9. The fluid sensor assembly of claim 1, wherein the header assembly includes a sensor circuit board, the sensor circuit board being electrically connected to the fluid quality sensor.

10. The fluid sensor assembly of claim 1, wherein the fluid quality sensor includes an ultrasound transducer in the sample tank for quality sampling of the fluid.

11. The fluid sensor assembly of claim 1, further comprising a fluid level sensor assembly separably coupled to the housing unit, the fluid level sensor assembly including a level sensor determining a fluid level of the fluid in the fluid tank, the fluid level sensor assembly including a fluid level sensor connector coupled to a sensor connector of the header assembly.

12. The fluid sensor assembly of claim 11, wherein the level sensor includes a reed switch.

13. The fluid sensor assembly of claim 11, wherein the fluid level sensor connector is coupled to the sensor connector of the header assembly at a separable interface.

14. The fluid sensor assembly of claim 1, further comprising a temperature control device coupled to the housing unit and configured to extend into the fluid tank, the temperature control device configured to be in thermal communication with the fluid in the fluid tank to affect a temperature of the fluid in the fluid tank.

15. The fluid sensor assembly of claim 14, wherein the temperature control device includes a heating element for heating the fluid in the fluid tank.

16. The fluid sensor assembly of claim 14, wherein the temperature control device includes a cooling element for cooling the fluid in the fluid tank.

17. A fluid sensor assembly for sensing a fluid contained in a fluid tank of a vehicle, the fluid sensor assembly comprising:
   a housing unit having a base plate configured to be coupled to the fluid tank, the housing unit including a sample suction line and a sample return line configured to be in fluid communication with the fluid in the fluid tank;
   a fluid level sensor assembly separably coupled to the housing unit, the fluid level sensor assembly including a level sensor determining a fluid level of the fluid in the fluid tank, the fluid level sensor assembly including a fluid level sensor connector; and
   a header assembly having a header housing separably coupled to the housing unit, the header housing configured to be located exterior of the fluid tank of the vehicle, the header assembly having a sensor connector coupled to the fluid level sensor connector to receive data from the fluid level sensor assembly relating to the fluid level measured by the fluid level sensor, the header assembly having a sample tank in fluid communication with the sample suction line and the sample return line, the sample tank located exterior of the fluid tank and configured to receive fluid from the fluid tank, the header assembly including a fluid quality sensor sensing a quality characteristic of the fluid in the sample tank for quality sampling of the fluid at a location remote from an interior of the fluid tank.

18. The fluid sensor assembly of claim 17, wherein the fluid level sensor assembly includes a float received in the fluid tank configured to float on top of the fluid, the level sensor measuring a position of the float to determine the fluid level of the fluid in the fluid tank.

19. A fluid sensor assembly for sensing a fluid contained in a fluid tank of a vehicle, the fluid sensor assembly comprising:
   a housing unit having a base plate configured to be coupled to the fluid tank, the housing unit including a sample suction line and a sample return line configured to be in fluid communication with the fluid in the fluid tank;
   a temperature control device coupled to the housing unit and configured to extend into the fluid tank, the temperature control device configured to be in thermal communication with the fluid in the fluid tank to affect a temperature of the fluid in the fluid tank; and
   a header assembly having a header housing separably coupled to the housing unit, the header housing configured to be located exterior of the fluid tank of the vehicle, the header assembly having a sample tank in fluid communication with the sample suction line and the sample return line, the sample tank located exterior of the fluid tank and configured to receive fluid from the fluid tank, the header assembly including a fluid quality sensor sensing a quality characteristic of the fluid in the sample tank for quality sampling of the fluid at a location remote from an interior of the fluid tank.

20. The fluid sensor assembly of claim 19, wherein the temperature control device includes at least one of a heating element for heating the fluid in the fluid tank and a cooling element for cooling the fluid in the fluid tank.

* * * * *